United States Patent
Wajima et al.

(10) Patent No.: US 9,681,837 B2
(45) Date of Patent: Jun. 20, 2017

(54) CENTRAL SENSITIZATION DIAGNOSIS DEVICE AND METHOD FOR OPERATING SAME

(71) Applicants: KEIO UNIVERSITY, Tokyo (JP); ICST CORPORATION, Saitama-shi, Saitama (JP)

(72) Inventors: Koichi Wajima, Tokyo (JP); Hitoshi Sato, Tokyo (JP); Hironori Saisu, Tokyo (JP); Wataru Muraoka, Tokyo (JP); Taneaki Nakagawa, Tokyo (JP); Yasunori Kato, Saitama (JP)

(73) Assignees: Keio University, Tokyo (JP); ICST Corporation, Saitama (JP)

( * ) Notice: Subject to any disclaimer, the term of this patent is extended or adjusted under 35 U.S.C. 154(b) by 0 days.

(21) Appl. No.: 14/379,701

(22) PCT Filed: Feb. 19, 2013

(86) PCT No.: PCT/JP2013/053976
§ 371 (c)(1),
(2) Date: Aug. 19, 2014

(87) PCT Pub. No.: WO2013/125518
PCT Pub. Date: Aug. 29, 2013

(65) Prior Publication Data
US 2015/0065909 A1     Mar. 5, 2015

(30) Foreign Application Priority Data

Feb. 20, 2012  (JP) .................................. 2012-033972

(51) Int. Cl.
*A61B 5/00*     (2006.01)
*A61F 7/00*     (2006.01)
*A61F 7/02*     (2006.01)

(52) U.S. Cl.
CPC ............ *A61B 5/483* (2013.01); *A61B 5/7282* (2013.01); *A61F 7/007* (2013.01); *A61F 2007/0075* (2013.01); *A61F 2007/0295* (2013.01)

(58) Field of Classification Search
CPC ........................................................ A61B 5/483
(Continued)

(56) References Cited

U.S. PATENT DOCUMENTS 7,399,281 B2 * 7/2008 Shimazu .............. A61B 5/4824
600/552
2005/0267338 A1   12/2005 Lipman
(Continued)

FOREIGN PATENT DOCUMENTS

EP     2 425 765 A2    3/2012
JP     H10-179591 A1   7/1998
(Continued)

OTHER PUBLICATIONS

Martucci et al. "Differential effects of experimental central sensitization on the time-course and magnitude of offset analgesia" Pain 153 (2012) 463-472 published online Dec. 6, 2011.*

(Continued)

*Primary Examiner* — Michael C Stout
(74) *Attorney, Agent, or Firm* — Leydig, Voit & Mayer, Ltd.

(57) ABSTRACT

An object of the present invention is to provide a system for performing objective examination of central sensitization, in particular, a system for objectively determining the presence or absence of central sensitization in a chronic pain patient. The present invention provides a device for diagnosing the presence or absence of central sensitization, the device including: stimulation output means for outputting thermal stimulation which can be perceived by a subject; first input
(Continued)

means capable of inputting a measurement start signal; second input means capable of inputting a measurement end signal; and measurement control means for measuring time between an input signal from the first input means and an input signal from the second input means. The measurement control means determines that the central sensitization is present when the time between the input signal from the first input means and the input signal from the second input means is longer than t seconds (where t represents 30 seconds or more and less than 90 seconds).

6 Claims, 3 Drawing Sheets

(58) Field of Classification Search
USPC .......................................................... 600/555
See application file for complete search history.

(56) References Cited

U.S. PATENT DOCUMENTS

| | | | |
|---|---|---|---|
| 2009/0196824 A1* | 8/2009 | Elman | A61K 31/519 424/9.1 |
| 2009/0227890 A1* | 9/2009 | Lanfermann | A61B 5/483 600/555 |
| 2009/0270757 A1* | 10/2009 | Backonja | A61B 5/483 600/555 |
| 2012/0109003 A1 | 5/2012 | Ordriozola Orlandi | |

FOREIGN PATENT DOCUMENTS

| | | |
|---|---|---|
| WO | 02/32304 A1 | 4/2002 |
| WO | WO 2010/112647 A2 | 10/2010 |

OTHER PUBLICATIONS

Greenspan et al. "Pain Sensitivity Risk Factors for Chronic TMD" The Journal of Pain, vol. 12, No. 11 Nov. 2011 pp. T61-T74.*
Martucci et al., "Differential Effects of Experimental Central Sensitization on the Time-course and Magnitude of Offset Analgesia," *Pain*, 153(2): 463-472 (2011).
Staud et al., : Temporal Summation of Pain from Mechanical Controls and Subjects with Fibromyalgia Syndrome, *Pain*, 102(1): 87-95 (2003).
European Patent Office, Supplementary European Search Report in European Patent Application No. 13751369 (Sep. 23, 2015).
Raphael et al., "Temporal Summation of Heat Pain in Temporomandibular Disorder Patients," *J. Orofac. Pain*, 23(1): 54-64 (2009).
Sato, "Gakukansetsuen Kanja ni Okeru Chusu Kansa no Hyoka" ("Evaluation of central sensitization in temporomandibular disorder patients—Analysis of central sensitization in TMD"), *Journal of Japanese Society for Temporomandibular Joint*, Dai 23 Kai Taikai special issue, 22: 96 (Jul. 2010).
Sato, "Togakubu no Kin•Kinmakusei Totsu ni Okeru Chusu Kansa no Hyoka" ("Evaluation of central sensitization in head and neck myofascial pain"), *Japanese Journal of Headache*, Dai 38 Kai Japanese Headache Society Sakai Program•Shorokushu, 37(2): 221, Abstract 19-C-22 (2010).
Japanese Patent Office, International Search Report in International Patent Application No. PCT/JP2013/053976 (Mar. 19, 2013).

* cited by examiner

CENTRAL SENSITIZATION DIAGNOSIS DEVICE AND METHOD FOR OPERATING SAME

CROSS-REFERENCE TO RELATED APPLICATION

This application claims priority from Japanese Patent Application No. 2012-033972, filed on Feb. 20, 2012, the entire disclosure of which is incorporated herein by reference.

TECHNICAL FIELD

The present invention relates to a device for diagnosing the presence or absence of central sensitization in a subject with chronic pain and a method of operating the device.

BACKGROUND ART

There has been known that, in chronic pain patients suffering from tension-type headache, temporomandibular disorder, and the like, a sensory nerve is sensitized in peripheral and central nervous systems, with the result that abnormalities such as hypersensitivity, increased responsiveness, and enlargement of receptive fields occur in some cases. When a peripheral nerve or a central nerve is sensitized with pain, pain is intensified, and a range of pain is enlarged. Consequently, a patient feels pain even in a site in which the patient does not usually feel pain. When central sensitization is caused by chronic headache, temporomandibular disorder, and the like, in most cases, symptoms are not alleviated even if standard therapies for original headache and temporomandibular disorder are conducted, and treatments using an antidepressant and the like acting on the central nervous system are required. At least several percentages of the patients with headache, temporomandibular disorder, and the like are considered to have such central sensitization, and treatments to be conducted totally vary depending on whether the patients have mere headache, temporomandibular disorder, and the like, or have central sensitization. Therefore, it is very important to diagnose the presence or absence of the central sensitization.

However, the central sensitization can be diagnosed only by, for example, a detailed medical interview performed by experienced physicians or confirmation of a response to mechanical stimulation, and hence the diagnosis thereof is not easy.

Consequently, in spite of the fact that a patient has central sensitization, the patient is diagnosed to have mere temporomandibular disorder or the like. Then, it is predicted that such a situation frequently occurs that, although provided with a therapy for temporomandibular disorder, the patient is not improved in the symptom and goes to another hospital for seeking a second opinion. This is considered to serve as a factor for so-called "doctor shopping" in which a patient visits various hospitals.

According to the US actual situation survey in 1998 to 1999, the ratio of patients suffering from chronic pain at a medium level or more is determined to be 9% of the adult population. Then, the social economic loss caused by the waste of medical fees caused by ineffective treatments and doctor shopping and difficulty in working due to pain and the like is estimated to be about 9 trillion yen per year.

Under such circumstances, there is a demand for establishing a quantitative sensory test (QST) as an objective examination method for central sensitization.

On the other hand, hitherto, patients with temporomandibular disorder and the like have been evaluated for temporal summation (TS) of pain sensation caused by continuous thermal stimulation. The TS is a phenomenon in which, in spite of the fact that thermal stimulation increasing or decreasing continuously is performed with a temperature width and stimulus sensation being constant, pain intensity felt by a subject increases gradually as the number of stimulation increases to 5 times, 10 times, and 15 times. Then, Non Patent Literature 1 discloses that, when such thermal stimulation is applied, aftersensations are caused in a test site even after the end of the stimulation. However, Non Patent Literature 1 merely evaluates the difference in aftersensations between a patient with temporomandibular disorder and a healthy subject and does not at all disclose a method of discriminating a temporomandibular disorder patient and a chronic temporomandibular disorder patient with central sensitization.

CITATION LIST

Non Patent Literature

[NPL 1] Raphael K G et al. J Orofac Pain. 2009; 23(1): 54-64.

SUMMARY OF INVENTION

Technical Problem

It is an object of the present invention to provide a system for performing objective examination of central sensitization, in particular, a system for objectively determining the presence or absence of central sensitization in a chronic pain patient.

Solution to Problem

Under the above-mentioned circumstances, as a result of the extensive studies, the inventors of the present invention have found that, when thermal stimulation is applied to a test site continuously, there is a significant difference in duration of aftersensations after the end of thermal stimulation between a patient with central sensitization and a patient without central sensitization among chronic pain patients with headache, temporomandibular disorder, and the like. The inventors of the present invention further have variously studied conditions such as the temperature, interval, and time of thermal stimulation based on the following new finding, thereby achieving the present invention.

Therefore, the present invention provides the following items.

Item 1. A device for diagnosing a presence or absence of central sensitization in a subject with chronic pain, the device comprising:

stimulation output means for outputting thermal stimulation which can be perceived by the subject with chronic pain;

first input means capable of inputting a measurement start signal;

second input means capable of inputting a measurement end signal; and measurement control means for measuring time between an input signal from the first input means and an input signal from the second input means.

Item 2. A device according to Item 1, wherein the measurement control means determines that the central sensitization is present when the time between the input signal from the first input means and the input signal from the second input means is longer than t seconds, where t represents 30 seconds or more and less than 90 seconds.

Item 3. A device according to Item 1 or 2, wherein the thermal stimulation includes thermal stimulation of 43° C. or more.

Item 4. A device according to any one of Items 1 to 3, wherein the thermal stimulation is performed by carrying out a temperature increase from a lower limit temperature t1 to an upper limit temperature t2 and a temperature decrease from the upper limit temperature t2 to the lower limit temperature t1 repeatedly n times, t1, t2, and n satisfying the following conditions:

$44 \leq t1 \leq 46;$ $46 \leq t2 \leq 48;$ and $9 \leq n \leq 13.$

Item 5. A device according to any one of Items 1 to 4, wherein the thermal stimulation is performed for 15 to 50 seconds in total.

Item 6. A method of operating a device, the method comprising the steps of:

applying thermal stimulation to a test site of a subject with chronic pain by stimulation output means;

receiving a measurement start signal from first input means by measurement control means;

receiving a measurement end signal from second input means by the measurement control means;

calculating time between an input signal from the first input means and an input signal from the second input means by the measurement control means; and determining that central sensitization is present when the time between the input signal from the first input means and the input signal from the second input means is longer than t seconds, where t is 30 seconds or more and less than 90 seconds, by the measurement control means.

Item 7. A method according to Item 6, wherein the stimulation output means generates heat of 43° C. or more.

Item 8. A method according to claim 6 or 7, wherein the stimulation output means is configured to carry out a temperature increase from a lower limit temperature t1 to an upper limit temperature t2 and a temperature decrease from the upper limit temperature t2 to the lower limit temperature t1 repeatedly n times, t1, t2, and n satisfying the following conditions:

$44 \leq t1 \leq 46;$ $46 \leq t2 \leq 48;$ and $9 \leq n \leq 13.$

Item 9. A method according to any one of Items 6 to 8, wherein the thermal stimulation is performed for 15 to 50 seconds in total.

Item 10. A method of diagnosing a presence or absence of central sensitization in a subject with chronic pain, the method comprising:

applying thermal stimulation to a test site of the subject with chronic pain; and measuring time from end of thermal stimulation to disappearance of aftersensations in the subject.

Item 11. A method according to Item 10, wherein it is determined that central sensitization is present when the time from the end of the thermal stimulation to the disappearance of aftersensations in the subject is longer than t seconds, where t represents 30 seconds or more and less than 90 seconds.

Item 12. A method according to Item 10 or 11, in which the thermal stimulation includes thermal stimulation at 43° C. or more.

Item 13. A method according to any one of Items 10 to 12, wherein the thermal stimulation is performed by carrying out a temperature increase from a lower limit temperature t1 to an upper limit temperature t2 and a temperature decrease from the upper limit temperature t2 to the lower limit temperature t1 repeatedly n times, t1, t2, and n satisfying the following conditions:

$44 \leq t1 \leq 46;$ $46 \leq t2 \leq 48;$ and $9 \leq n \leq 13.$

Item 14. A method according to any one of Items 10 to 13, wherein the thermal stimulation is performed for 15 to 50 seconds in total.

Advantageous Effects of Invention

The presence or absence of central sensitization in a chronic pain patient can be objectively determined through use of the device of the present invention. Further, according to one embodiment of the present invention, central sensitization can be determined with both high sensitivity and high specificity. Herein, the sensitivity refers to a probability for determining what is to be determined to be positive to be positive correctly (probability for correctly determining a patient with central sensitization to have central sensitization in the case of the present invention). Further, the specificity refers to a probability for determining what is to be determined to be negative to be negative correctly (probability for correctly determining a patient without central sensitization not to have central sensitization in the case of the present invention).

DESCRIPTION OF EMBODIMENTS

Figure 1:
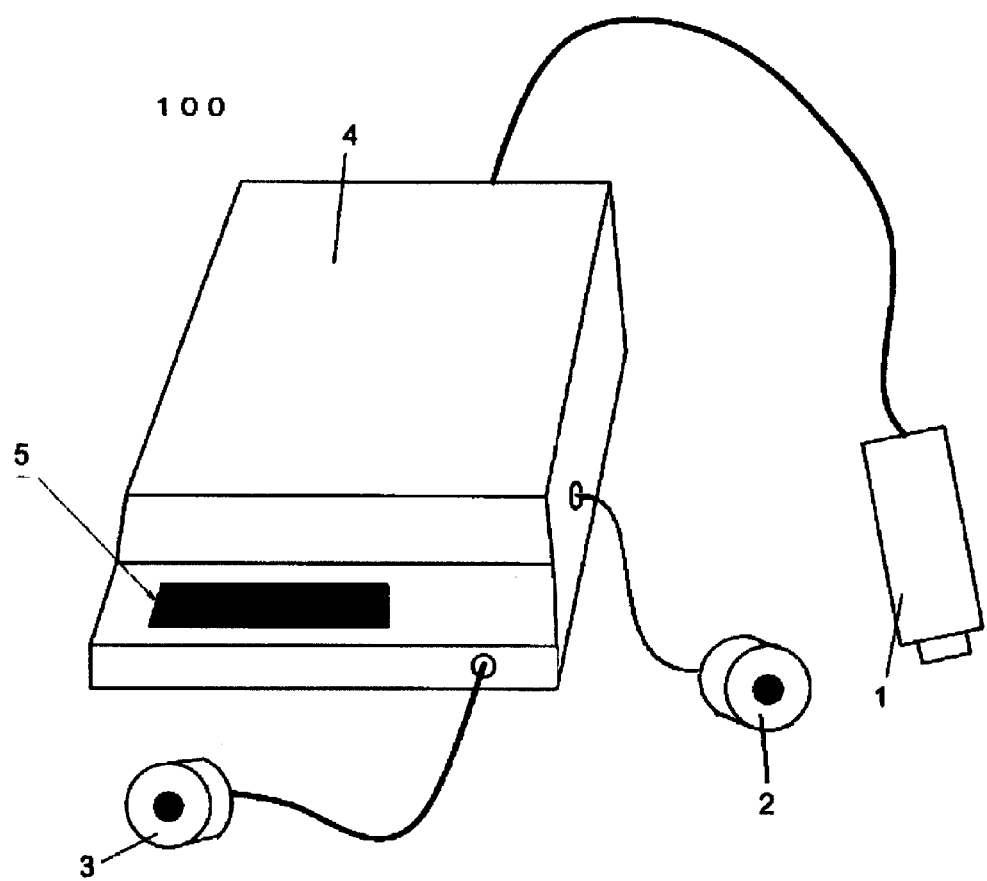
FIG. 1 is a schematic structural view of a central sensitization diagnosis device 100 according to an embodiment of the present invention.

Now, the present invention is described with reference to the drawings. However, the present invention is not limited to an embodiment described in the drawings.

FIG. 1 is a schematic structural view of a central sensitization diagnosis device 100 according to an embodiment of the present invention. As illustrated in FIG. 1, the central sensitization diagnosis device 100 includes stimulation output means 1 for outputting thermal stimulation which can be perceived by a subject with chronic pain, first input means 2 capable of inputting a measurement start signal, second input means 3 capable of inputting a measurement end signal, and measurement control means 4 for measuring time between an input signal from the first input means 2 and an input signal from the second input means 3. The stimulation output means 1, the first input means 2, and the second input means 3 are each connected to the measurement control means 4 through cords and can transmit/receive a signal to/from the measurement control means 4.

Figure 2:
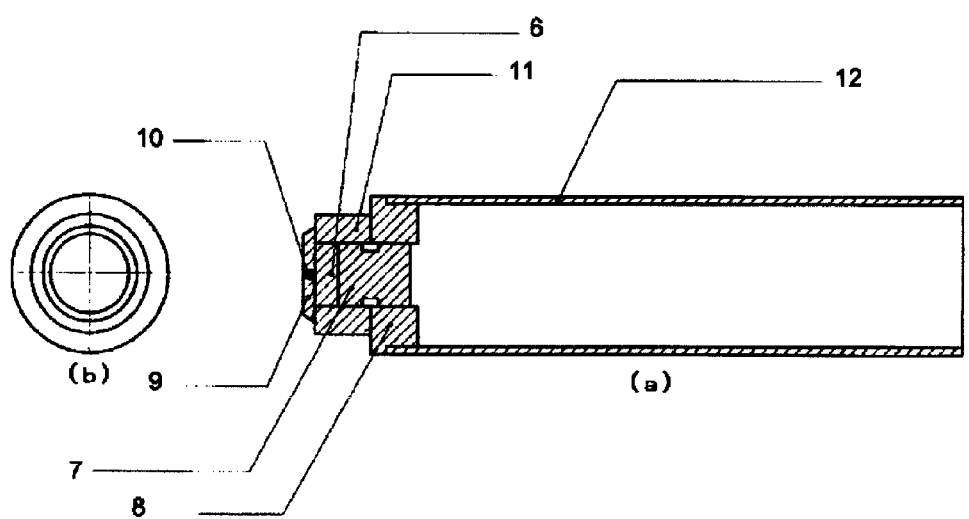
FIG. 2(a) is a sectional view of stimulation output means 1.
FIG. 2(b) is a front view thereof.

FIG. 2(*a*) is a sectional view of the stimulation output means 1 and FIG. 2(*b*) is a front view thereof. As illustrated in FIG. 2, the stimulation output means 1 includes a body case 12 which can be held by a hand and radiation blocks 7, 8 fixed to an end of the body case 12. Further, the stimulation output means 1 includes a heat-generation member 6 and a heat-insulation block 11 fixed to ends of the radiation blocks 7, 8 and a thermal stimulation plate 9 fixed to an end of the heat-generation member 6.

The heat-radiation blocks 7, 8 are formed of, for example, a material having heat conductivity such as a metal and are in contact with the heat-generation member 6 so as to release heat generated in the heat-generation member 6 to the outside. Further, the heat-insulation block 11 is formed of a material having heat insulation and is disposed so as to surround the periphery of the heat-generation member 6.

As the heat-generation member 6, for example, there are given a Peltier module (element for heating or cooling in accordance with a direction of a current, which may be simply referred to as a "Peltier" herein), and an electric heater. A Peltier module is preferred because it is capable of regulating temperature minutely.

Although the temperature of the above-mentioned thermal stimulation can be appropriately set depending on the area, time, and the like for applying thermal stimulation, for example, the temperature can be set in a range of 43° C. or more (for example, 44° C. or more, 45° C. or more, etc.). In general, when thermal stimulation at 43° C. or more is applied to a subject, the subject feels pain. Hitherto, in order to check the difference in aftersensations between a patient with temporomandibular disorder and a healthy subject, a method involving increasing or decreasing temperature periodically around 43° C., specifically between a lower limit temperature less than 43° C. and an upper limit temperature more than 43° C. has been used. However, in the diagnosis of central sensitization according to the present invention, it is preferred that thermal stimulation be applied continuously for a predetermined period of time at a temperature equal to or more than 43° C. which is higher than that of the conventional thermal stimulation, because aftersensations do not remain more than necessary, and rather the presence or absence of central sensitization can be determined with good sensitivity and specificity.

Although thermal stimulation at constant temperature may be used, thermal stimulation by repeating thermal stimulation at high temperature and low temperature (the thermal stimulation may be hereinafter simply referred to as continuous thermal stimulation, repetitive thermal stimulation, or the like) is preferred because it suppresses invasiveness with respect to a test site and gives required stimulation. More specifically, for example, it is preferred that the above-mentioned thermal stimulation be given so as to increase or decrease temperature periodically between a lower limit temperature t1 and an upper limit temperature t2. For example, it is preferred that the thermal stimulation be performed by carrying out a temperature increase from the lower limit temperature t1 to the upper limit temperature t2 and a temperature decrease from the upper limit temperature t2 to the lower limit temperature t1 repeatedly n times (In this case, it is preferred that t1, t2, and n satisfy the following conditions: $44 \leq t1 \leq 46$; $46 < t2 \leq 48$; and $9 \leq n \leq 13$. It is more preferred that t1, t2, and n satisfy the following conditions: $44.5 \leq t1 \leq 45.5$; $46.5 \leq t2 \leq 47.5$; and $10 \leq n \leq 12$). The above-mentioned step of "carrying out the temperature increase from the lower limit temperature t1 to the upper limit temperature t2 and the temperature decrease from the upper limit temperature t2 to the lower limit temperature t1 repeatedly n times" also includes an embodiment of keeping the temperature t2 for a predetermined period of time (for example, 2 seconds or less, more preferably 0.5 to 1.5 seconds) between the temperature increase from the lower limit temperature t1 to the upper limit temperature t2 and the temperature decrease from the upper limit temperature t2 to the lower limit temperature t1. For example, there is given a method of repeatedly carrying out the following: increasing temperature from 45° C. to 47° C. in 1 second, keeping 47° C. for 1 second, and thereafter decreasing the temperature to 45° C. in 1 second. The time during which such thermal stimulation is given may vary depending on the temperature of thermal stimulation and the like. However, from the viewpoint that the length of the time is sufficient for aftersensations required for diagnosis of central sensitization to remain for a predetermined period of time, and the invasiveness with respect to a subject is not too high, for example, the thermal stimulation is given for preferably a total of 15 to 50 seconds, more preferably a total of 30 to 35 seconds.

In the embodiment in which thermal stimulation is given repeatedly, the measurement control means 4 is configured so as to control such thermal stimulation. More specifically, for example, the heat-generation temperature of the heat-generation member 6 can be regulated by regulating a voltage to be applied to the heat-generation member 6 along with the passage of time by the measurement control means 4. Thus, thermal stimulation can be repeatedly applied to a subject. Herein, it is preferred to set the period at which thermal stimulation is given repeatedly to be constant as described above because the temperature control becomes easy and as a result, the device can be downsized to be less expensive.

Further, the thermal stimulation plate 9 is a member which is brought into contact with a test site of a subject and is disposed so as to cover an end of the heat-generation member 6 so that the test site and the heat-generation member 6 do not come into direct contact with each other. Thus, the device becomes stronger to thermal disturbance when the thermal stimulation plate 9 having a heat capacity is interposed as a buffer between the test site and the outside air, and the heat-generation member 6, compared to when the heat-generation member 6 is brought into direct contact with the test site. Although there is no particular limit to an area of a surface, with which the test site and the thermal stimulation plate 9 come into contact, the area is set to be preferably 0.125 to 1.0 cm$^2$, more preferably 0.25 to 0.5 cm$^2$ so as to prevent excess heating and to give thermal stimulation required for examination to the test site.

Further, a temperature sensor 10 may be disposed in the thermal stimulation plate 9. In the case of disposing the temperature sensor 10, a place where the temperature sensor 10 is to be disposed is not particularly limited as long as the temperature of the thermal stimulation plate 9 can be measured; it is preferred that the temperature sensor 10 be disposed in the thermal stimulation plate 9 because such arrangement of the temperature sensor 10 enables more precise temperature control.

In this embodiment, the first input means 2 is formed of a press button, and a measurement start signal can be input by pressing the button. The measurement start signal can be input, for example, by a physician. In this case, the measurement start signal is input at a time of the end of thermal stimulation.

In this embodiment, the second input means 3 is formed of a press button, and a measurement end signal can be input by releasing the pressing of the button or pressing the button. The measurement end signal can be input by a subject. In this case, the measurement start signal is input at a time of the end of thermal stimulation. The subject inputs the above-mentioned measurement end signal at a time when the subject does not feel aftersensations caused by thermal stimulation any more. There is no particular limit to a system of inputting a signal from the subject as long as time from the end of thermal stimulation to the disappearance of aftersensations can be measured. Any of the following systems may be used: a system in which a subject continues to press the second input means 3 while feeling aftersensations after the end of stimulation and detaches the hand from the second input means 3 when the subject does not feel aftersensations anymore; and a system in which the subject does not press the second input means 3 while feeling aftersensations, and presses the second input means 3 at a time when the subject does not feel aftersensations any more.

The measurement control means 4 is configured so as to measure time between both input signals by receiving an input signal from the first input means 2 and receiving an input signal from the second input means 3. Further, the measurement control means 4 is configured so as to determine that central sensitization is present in the case where the time between the input signal from the first input means 2 and the input signal from the second input means 3 is more than t seconds and determine that central sensitization is absent in the case where the time is less than t seconds.

Herein, a threshold value (cut-off value) t can be appropriately set depending on the temperature and time of thermal stimulation, the age and sex of a patient, etc. However, the threshold value t is set to 30 seconds or more and less than 90 seconds, preferably in a range of 45 to 60 seconds. Thus, the present invention also includes, for example, a method in which the threshold value t is set to 30 seconds and a method in which the threshold value t is set to 60 seconds. It is preferred to set the time in the above-mentioned range in advance because a patient with central sensitization can be determined exactly from those with temporomandibular disorder and headache with high sensitivity and high specificity.

Further, a diagnosis table in which a threshold value t for each age and sex of a patient is set may be prepared in advance, and the information thereof may be input to the measurement control means. In this case, during measurement, the presence or absence of central sensitization is determined by inputting an age and a sex of a patient, measuring the duration of aftersensations, and applying the information to the diagnosis table.

Further, the measurement control means 4 may include display means 5 for displaying measured time. As the display means 5, for example, a known liquid crystal display or the like can be used. The present invention provides the above-mentioned device. Note that, the device of the present invention can also be referred to as a system including each of the above-mentioned means.

Method of Operating Device

Next, a method of operating the central sensitization diagnosis device 100 configured as described above is described.

First, the stimulation output means gives thermal stimulation to a test site of a subject with chronic pain. More specifically, the thermal stimulation plate 9 of the stimulation output means 1 is brought into contact with the test site of the subject while the heat-generation member 6 is generating heat, and the thermal stimulation plate 9 is kept in contact with the test site for a predetermined period of time (for example, about 3 seconds). Alternatively, the heat-generation member 6 is caused to generate heat after the thermal stimulation plate 9 of the stimulation output means 1 is brought into contact with the test site of the subject, and the contact state between the thermal stimulation plate 9 and the test site is kept for a predetermined period of time. Thus, thermal stimulation can be given to the subject. Examples of the test site of the subject include an arm, the back of a hand, a leg, and a facial surface.

Next, after the passage of the above-mentioned predetermined period of time (for example, about 3 seconds), thermal stimulation with respect to the subject is ended by detaching the thermal stimulation plate 8 from the subject or decreasing the temperature of the heat-generation member to less than predetermined temperature (for example, the above-mentioned lower limit temperature t2). Further, along with this, a measurement start signal is input by pressing the press button of the first input means 2. When the measurement start signal is input from the first input means 2, the measurement control means 4 starts measuring time.

Subsequently, when the subject does not feel aftersensations any more, the subject inputs a measurement end signal by detaching the hand from the second input means 3 or by pressing the press button. When the measurement end signal is input from the second input means 3, the measurement control means 4 ends measuring time. Thus, the measurement control means 4 can measure time between the input signal from the first input means 2 and the input signal from the second input means 3. The measured time is displayed on the display means 5 as necessary.

Further, the measurement control means 4 can determine the following based on the measured time and display the determination result on the display means 5. That is, the measurement control means 4 determines that central sensitization is present in the case where the time between the input signal from the first input means and the input signal from the second input means is longer than the predetermined time t seconds. Herein, the threshold value t is as described above.

The embodiment of the present invention has been described above. However, the present invention is not limited to the embodiment.

For example, the stimulation output means 1, the first input means 2, and/or the second input means 3 may not be connected to the measurement control means 4 through cords and send each signal to the measurement control means 4 wirelessly. Further, the first input means 2 may be integrated with the stimulation output means 1 or the measurement control means 4.

Further, in the above-mentioned embodiment, the first input means 2 has a press button configuration; however, the configuration thereof is not particularly limited as long as the first input means 2 can input a measurement start signal. For example, the first input means 2 may have a configuration of a contact sensor set in the stimulation output means 1. In this case, the first input means 2 (sensor) is configured so as to detect contact/non-contact of the thermal stimulation plate 9 with respect to the subject and send a measurement start signal to the measurement control means 4 when the thermal stimulation plate 9 takes a non-contact state.

Further, for example, the first input means 2 may have the following configuration: the first input means 2 is incorporated in the stimulation output means 1 and sends temperature information from the temperature sensor to the measurement control means; after the end of predetermined temperature stimulation (for example, at a time when the temperature becomes less than the lower limit temperature t1 after the thermal stimulation is repeated n times), the first input means 2 sends a start signal and the measurement control means 4 starts measurement.

The above-mentioned embodiment is configured so that, in the case where thermal stimulation is given repeatedly, the measurement control means 4 controls the thermal stimulation. However, the device may include another control means 4' separately from the measurement control means 4, and the control means 4' may control thermal stimulation. This embodiment is configured so that the measurement control means 4 measures time between the input signal from the first input means and the input signal from the second input means, and the control means 4' controls thermal stimulation. In this case, the measurement control means 4 and the control means 4' may be or may not be connected through a cord or the like. Then, the control means 4' may be connected to the stimulation output means 1 or may be incorporated in the stimulation output means 1.

Figure 3:
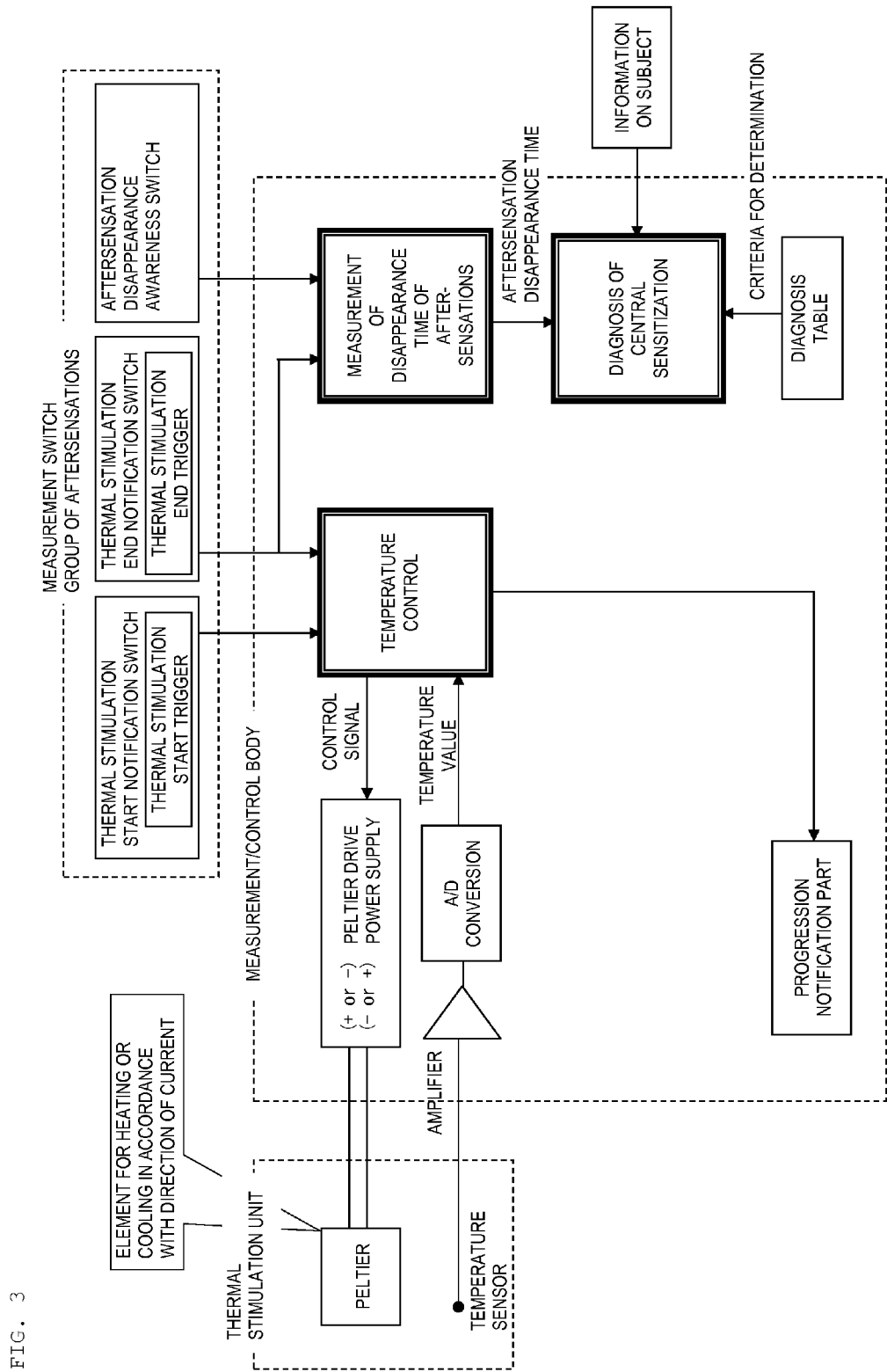
FIG. 3 is a block diagram of a method of operating the device according to the embodiment of the present invention.

Further, the stimulation output means 1 described above may further include a thermal simulation start switch and a thermal stimulation end switch. The thermal stimulation start switch and the thermal stimulation end switch are not limited to physical switches. The following system may be used. Specifically, a contact sensor serving as the thermal stimulation start switch is integrated with the stimulation output means 1 and the stimulation output means 1 is brought into contact with the subject so that a signal is input to the thermal stimulation start switch, and the signal is sent to the measurement control means 4. Note that, for reference, FIG. 3 illustrates a block diagram of a method of operating the device according to the embodiment of the present invention.

EXAMPLES

Example 1

Target

Ten people diagnosed to have chronic pain in the masticatory muscle were classified into a patient group and a control group to be tested as follows.

Patient group: 5 patients who were diagnosed to have myofascial pain and clinically evaluated to have central sensitization among chronic temporomandibular disorder patients with masticatory muscle disorder for 3 months or more Control group: 5 patients who were not clinically evaluated to have central sensitization among chronic temporomandibular disorder patients with localized myalgic pain in the masticatory muscle Herein, the diagnosis of myofascial pain in the masticatory muscle and localized myalgic pain in the masticatory muscle was conducted based on the following criteria in accordance with the classification of International Headache Society (IHS) and International Classification of Disease (ICD).

Criteria for Diagnosis of Myofascial Pain in Masticatory Muscle (IHS 11.7.2.1: ICD-9 729.1)

All of the following is recognized in the masticatory muscle.

1. Local dull and aching pain at rest
2. Pain is worsened due to activities of affected muscle
3. Stimulation to a trigger point by frequent palpation of cord-like induration in a muscle tissue or fascia changes the complaint of pain and frequently shows a pattern of referred pain.
4. Reduction of pain by more than 50% due to a cooling spray or local analgesic injection to a trigger point and the subsequent extension Criteria for Diagnosis of Localized Myalgic Pain in Masticatory Muscle (IHS 11.7.2.2: ICD-9 729.1)

All of the following is recognized in masticatory muscle

1. Local dull or aching pain which is functioning in affected muscle
2. Reduction or disappearance of pain at rest
3. Tenderness caused by palpation of localized muscle
4. There are no trigger point and referred pain caused by the trigger point The clinical diagnosis of central sensitization was conducted by the following method.

Clinical Evaluation Method for Central Sensitization

Patients who were recognized to correspond to all of the following and diagnosed to suffer from central sensitization by a detailed medical interview by an experienced physician were classified as a patient group:

1. The state in which a sensory threshold value of an affected part has decreased or the state in which pain has been induced by stimulation which may not usually induce pain was observed through use of a Von fry.
2. Pain stronger than pain sensation felt usually is felt due to the pain stimulation through use of a Pin Prick.
3. The foregoing two points are also observed in another innervation area which is not a nerve controlling an affected site.

[Test Method]

Thermal stimulation output means (area of a thermal stimulation plate: 0.28 cm$^2$) was brought into contact with each facial surface part and each arm part of a patient group and a control group, and thermal stimulation of increasing the temperature from 45° C. to 47° C. in 1 second, keeping the temperature of 47° C. for 1 second, and decreasing the temperature to 45° C. in 1 second was applied to those groups repeatedly 11 times for a total of 33 seconds. After the end of the thermal stimulation, the duration of sensations remaining in a test site (aftersensations) was measured, and the difference between those groups was checked and considered statistically. A time when the temperature of the thermal stimulation plate reached 45° C. or less after the above-mentioned 11 thermal stimulations was defined as a start time of aftersensations, and a time when each subject gave a signal indicating the disappearance of the aftersensations was defined as an end time. A period of time between the start time and the end time was defined as duration. As described above, a facial surface (trigeminal innervation area) which is an affected site and an arm part which is a non-trigeminal innervation area are defined as test sites.

[Results]

The following Table 1 shows the results.

TABLE 1

| Patient group | Duration of aftersensations (sec) | | Control group | Duration of aftersensations (sec) | |
|---|---|---|---|---|---|
| | Facial surface | Arm | | Facial surface | Arm |
| 1 | 135 | 90 | 1 | 15 | 15 |
| 2 | 165 | 195 | 2 | 60 | 60 |
| 3 | 120 | 180 | 3 | 15 | 15 |
| 4 | 45 | 45 | 4 | 15 | 15 |
| 5 | 75 | 90 | 5 | 15 | 30 |
| Average | 108 | 120 | Average | 24 | 27 |

As is understood from the above results, the average duration of aftersensations in the patient group was significantly longer than that of the control group in the facial part which was an affected site, and the similar results were also obtained in the arm part which was a non-trigeminal innervation area (Facial surface: t-test $P=0.014$, Arm: t-test $P=0.029$).

Example 2

Target

Of the patients with chronic temporomandibular disorder having masticatory muscle disorder for 3 months or more (including those having myofascial pain and localized myalgic pain), 18 patients in which the presence or absence of central sensitization was not evaluated clinically were targeted.

The criteria for diagnosis of temporomandibular disorder patients with masticatory muscle disorder (including those having myofascial pain and localized myalgic pain) were based on Example 1.

[Method]

In the same way as in Example 1, thermal stimulation of increasing the temperature from 45° C. to 47° C. in 1 second, keeping the temperature of 47° C. for 1 second, and decreasing the temperature to 45° C. in 1 second is applied to each facial surface part and arm part of the 18 patients repeatedly 11 times, and thereafter, duration of sensations remaining in a tested site (aftersensations) is measured. The presence or absence of central sensitization was clinically evaluated after the duration of aftersensations was measured. The evaluation of central sensitization based on the duration of aftersensations and the evaluation of clinical central sensitization were compared and studied.

A duration cut-off value for evaluating central sensitization through use of the duration of aftersensations instead of the clinical evaluation of central sensitization was studied (in the case where the duration exceeds a cut-off value, central sensitization is determined to be present, and in the case where the duration is a cut-off value or less, central sensitization is determined to be absent. A plurality of cut-off values were set, and an optimum cut-off range for appropriately evaluating central sensitization from each sensitivity and specificity was determined.

The clinical evaluation method for central sensitization is based on Example 1. A facial surface (trigeminal innervation area) which is an affected site and an arm part which is a non-trigeminal innervation area are defined as test sites.

[Results]

TABLE 2

| Patient No. | Duration of aftersensations (sec) | | Clinical evaluation of presence or absence of central sensitization |
|---|---|---|---|
| | Facial surface | Arm | |
| 1 | 45 | 15 | No |
| 2 | 45 | 15 | No |
| 3 | 135 | 90 | Yes |
| 4 | 15 | 30 | No |
| 5 | 30 | 30 | Yes |
| 6 | 195 | 90 | Yes |
| 7 | 90 | 90 | Yes |
| 8 | 45 | 30 | No |
| 9 | 15 | 15 | No |
| 10 | 15 | 15 | No |
| 11 | 90 | 90 | Yes |
| 12 | 15 | 60 | Yes |
| 13 | 15 | 15 | No |
| 14 | 195 | 225 | Yes |
| 15 | 195 | 90 | Yes |
| 16 | 15 | 30 | No |
| 17 | 15 | 15 | No |
| 18 | 15 | 45 | No |

As a result of the clinical evaluation of central sensitization, as shown in Table 2, 8 out of 18 chronic temporomandibular disorder patients were clinically evaluated to have central sensitization. Of those 8 patients, the duration of aftersensations was 60 seconds or more in the arm part in 7 patients, and the duration of aftersensations was 60 seconds or more in both the facial part and the arm part in 6 patients. On the other hand, 10 patients were clinically evaluated not to have central sensitization. In all the 10 patients, the aftersensations disappeared from both the facial surface part and the arm part within 45 seconds.

Herein, the sensitivity and specificity in the case of evaluating central sensitization based on the duration of aftersensations were calculated based on the clinical evaluation of central sensitization, with the cut-off value being set to 30, 45, 60, 75, and 90 seconds. The results are shown below.

TABLE 3

| Cut-off value (sec) | Facial surface | | Arm | |
|---|---|---|---|---|
| | Sensitivity | Specificity | Sensitivity | Specificity |
| 30 | 0.75 | 0.7 | 0.875 | 0.9 |
| 45 | 0.75 | 1.0 | 0.875 | 1.0 |
| 60 | 0.75 | 1.0 | 0.75 | 1.0 |
| 75 | 0.75 | 1.0 | 0.75 | 1.0 |
| 90 | 0.5 | 1.0 | 0.125 | 1.0 |

The cut-off value in a method of diagnosing chronic pain caused in an orofacial area is generally set in a range so that the sensitivity and specificity thereof become at least 0.7 (Okeson J P. Orofacial Pain: Guidelines for Assessment, Diagnosis, and Management, $2^{nd}$ edn, Chicago: Quintessence, 1996: 137-141). Thus, although the setting of the range of the cut-off value in this examination needs to be appropriately considered depending on the temperature and time of thermal stimulation, the age and sex of a patient, and the like, the cut-off value is set to preferably 30 seconds or more and less than 90 seconds, more preferably in a range of 45 to 60 seconds.

Example 3

The duration of aftersensations was measured in the same way as in Example 1 except that thermal stimulation was applied to 5 subjects classified as a control group based on the same criteria as that of Example 1 repeatedly 13 times for a total of 39 seconds. Table 4 shows the results.

TABLE 4

| | Duration of aftersensations (sec) | |
|---|---|---|
| | Facial surface | Arm |
| 1 | 14 | 6 |
| 2 | 31 | 22 |
| 3 | 16 | 9 |
| 4 | 8 | 4 |
| 5 | 11 | 23 |

As is apparent from Table 4, it is understood that the duration of aftersensations is short in the control group even in the case where thermal stimulation is repeated 13 times which is larger than the repeated number of Example 1.

Example 4

The duration of aftersensations was measured in the same way as in Example 1 except that thermal stimulation was applied to 5 subjects classified as a patient group based on the same criteria as that of Example 1 repeatedly 9 times for a total of 27 seconds. Table 5 shows the results.

TABLE 5

| | Duration of aftersensations (sec) | |
|---|---|---|
| | Facial surface | Arm |
| 1 | 84 | 73 |
| 2 | 64 | 46 |
| 3 | 84 | 95 |
| 4 | 67 | 83 |
| 5 | 23 | 36 |

As is apparent from Table 5, it is understood that the duration of aftersensations is long in the patient group even in the case where thermal stimulation is repeated 9 times which is shorter than the repeated number of Example 1.

INDUSTRIAL APPLICABILITY

The use of the device of the present invention allows even less-experienced physician to easily determine the presence or absence of central sensitization in a chronic pain patient. The device for diagnosing the presence or absence of central sensitization precisely leads to the reduction of doctor shopping and then the reduction in medical fees, and hence there is a strong demand for such device. Accordingly, the device of the present invention is very useful in the medical field and the field of medical equipment to which the present invention belongs.

REFERENCE SIGNS LIST

1 stimulation output means, 2 first input means, 3 second input means, 4 measurement control means, 5 display means, 6 heat-generation member, 7 radiation block, 8 radiation block, 9 thermal stimulation plate, 10 temperature sensor, 11 heat-insulation block, 12 body case

The invention claimed is:

1. A device for diagnosing a presence or absence of central sensitization in a subject with chronic pain, the device comprising:
   stimulation output means for outputting thermal stimulation which can be perceived by the subject with chronic pain;
   first input means capable of inputting a measurement start signal at a time corresponding to the end of thermal stimulation;
   second input means capable of inputting a measurement end signal at a time when the subject does not feel aftersensations caused by the thermal stimulation; and
   a measurement control body configured to receive the measurement start signal from the first input means, to receive the measurement end signal from the second input means and to measure a time between the measurement start signal and the measurement end signal;
   wherein the measurement control body determines that the central sensitization is present when the time between the measurement start signal and the measurement end signal is longer than t seconds, where t represents 30 seconds or more and less than 90 seconds.

2. A device according to claim 1, wherein the thermal stimulation comprises thermal stimulation at 43° C. or more.

3. A device according to claim 1, wherein the thermal stimulation is performed by carrying out a temperature increase from a lower limit temperature t1 to an upper limit temperature t2 and a temperature decrease from the upper limit temperature t2 to the lower limit temperature t1 repeatedly n times,
   t1, t2, and n satisfying the following conditions:

$44 \leq t1 \leq 46$;

$46 \leq t2 \leq 48$; and $9 \leq n \leq 13$.

4. A method of operating a device, the method comprising the steps of:
   applying thermal stimulation to a test site of a subject with chronic pain by stimulation output means;
   receiving a measurement start signal from first input means by a measurement control body, wherein the first input means is configured to input the measurement start signal at a time corresponding to the end of thermal stimulation;
   receiving a measurement end signal from second input means by the measurement control body, wherein the second input means is configured to input the measurement end signal at a time when the subject does not feel aftersensations caused by the thermal stimulation; and
   calculating a time between an input signal from the first input means and an input signal from the second input means by the measurement control body, wherein the measurement control body is configured to receive the measurement start signal from the first input means, to receive the measurement end signal from second input means and to measure a time between the measurement start signal and the measurement end signal; and
   determining, by the measurement control body, that central sensitization is present when the time between the measurement start signal and the measurement end signal is longer than t seconds, where t represents 30 seconds or more and less than 90 seconds.

5. A method according to claim 4, wherein the stimulation output means generates heat of 43° C. or more.

6. A method according to claim 4, wherein the stimulation output means is configured to carry out a temperature increase from a lower limit temperature t1 to an upper limit temperature t2 and a temperature decrease from the upper limit temperature t2 to the lower limit temperature t1 repeatedly n times, t1, t2, and n satisfying the following conditions:

$44 \leq t1 \leq 46;$ $46 \leq t2 \leq 48;$ and $9 \leq n \leq 13.$

\* \* \* \* \*